(12) United States Patent
Ghosh

(10) Patent No.: US 10,058,732 B2
(45) Date of Patent: Aug. 28, 2018

(54) YOGA DEVICE

(76) Inventor: Ashim Ghosh, New Delhi (IN)

( * ) Notice: Subject to any disclaimer, the term of this patent is extended or adjusted under 35 U.S.C. 154(b) by 659 days.

(21) Appl. No.: 13/320,971

(22) PCT Filed: Jun. 5, 2009

(86) PCT No.: PCT/IN2009/000323
§ 371 (c)(1),
(2), (4) Date: Nov. 17, 2011

(87) PCT Pub. No.: WO2010/140158
PCT Pub. Date: Dec. 9, 2010

(65) Prior Publication Data
US 2012/0065024 A1 Mar. 15, 2012

(51) Int. Cl.
*A63B 23/18* (2006.01)
*A61M 21/00* (2006.01)

(52) U.S. Cl.
CPC ............. *A63B 23/18* (2013.01); *A61M 21/00* (2013.01); *A61M 2021/0088* (2013.01); *A61M 2205/8206* (2013.01); *A63B 2230/40* (2013.01)

(58) Field of Classification Search
CPC ....... A63B 23/18; A63B 23/185; A63B 23/03; G02C 5/122
USPC ............................................. 482/13; 606/151
See application file for complete search history.

(56) References Cited

U.S. PATENT DOCUMENTS

| 2,015,617 A | * | 9/1935 | Claudius | A62B 9/06 128/201.18 |
| 2,057,287 A | * | 10/1936 | Balley | G02C 5/124 351/132 |
| 4,231,360 A | * | 11/1980 | Zloczysti | A62B 9/06 128/201.18 |
| 4,504,892 A | | 3/1985 | Zulfilar | |
| 5,159,359 A | * | 10/1992 | Pauly | G02C 5/124 351/124 |
| 5,499,063 A | * | 3/1996 | Butler | A61B 3/04 351/41 |
| 5,533,504 A | * | 7/1996 | Stamos | A61F 5/56 128/200.24 |
| 6,215,409 B1 | | 4/2001 | Blach | |
| 6,302,103 B1 | * | 10/2001 | Resnick | A62B 9/06 128/201.23 |
| 6,788,011 B2 | | 9/2004 | Mueller et al. | |

(Continued)

FOREIGN PATENT DOCUMENTS

EP 0534710 B1 1/1996
WO 2008027174 A1 3/2008

*Primary Examiner* — Nyca T Nguyen
(74) *Attorney, Agent, or Firm* — Mark M. Friedman

(57) ABSTRACT

A device, for performing certain ancient yogic breathing practices of Pranayam without involving the use of hands, is controlled by a programmable controlling unit. The device is integrated onto the frame of a supporting base, worn on the nose, and uses battery-operated artificial fingers to block or unblock nostrils in programmable patterns, cycles and durations. This facilitates a precise and hands-free routine of alternate nostril breathing or single nostril breathing, in the most precise style, following techniques of ancient yogic Pranayam. The sensors of the device sense/measure the force and flow of the breath into and out of each nostril, and can automate and synchronize the artificial fingers to the normal breathing pattern of the user.

6 Claims, 7 Drawing Sheets

(56) References Cited

U.S. PATENT DOCUMENTS

| | | | |
|---|---|---|---|
| 6,801,003 B2 | 10/2004 | Schanberger et al. | |
| 7,038,398 B1 | 5/2006 | Lys et al. | |
| 7,380,934 B1 * | 6/2008 | Wang Lee | G02C 5/122 351/136 |
| 8,562,384 B2 * | 10/2013 | Vallejo | A63B 33/00 2/206 |
| 2002/0101561 A1 * | 8/2002 | Miceli | G02C 5/005 351/68 |
| 2009/0205642 A1 * | 8/2009 | McDevitt | A61F 5/08 128/200.24 |

* cited by examiner

YOGA DEVICE

This application is a National Phase entry of PCT International Application, Ser. No. PCT/IN2009/000323, filed Jun. 5, 2009, which is incorporated herein by reference.

FIELD OF TECHNOLOGY

This disclosure relates generally to health equipment and more particularly to a device for facilitating the performance of certain Yogic breathing practices.

BACKGROUND

Yogic practices have been followed since ancient times because of their positive impact on human health and well being. The certain Yogic breathing practices; eg. anulom vilom pranayam; are performed with the assistance of one hand's fingers used to block or unblock nostrils while breathing. This means at least one hand is thus engaged, and one may be able to not do other tasks that require the use of either both hands, or the occupied hand, hi addition, one has to remain focused to keep track of the breathing patterns and count the number of cycles specific to the technique being practiced. Thus most other tasks that require focus and attention cannot be performed, since incorrect patterns or number of cycles during yogic breathing may not be very effective.

In light of the foregoing discussion, there is a need for a device (and a manufacturing method thereof) that is suitable for facilitating the performance of certain yogic breathing practices without the use of hands, and which can be programmed or automated to perform specific patterns and cycles of certain yogic breathing techniques, while still achieving the desired outcome.

SUMMARY

An object of the present invention is to provide a device (and a manufacturing method thereof) that can be used to facilitate the performance of certain yogic breathing practices without the use of hands.

Another object of the present invention is to provide a device that can facilitate the performance of these yogic practices correctly, without reducing their benefits. Still another object of the present invention is to provide a device that includes minimum components.

Still another object of the present invention is to provide a device that can be programmed for desired need.

Still another object of the present invention is to provide a device that can be integrated with a range of portable devices, medical equipment and other diagnostic hardware and software.

Still another object of the present invention is to provide a device that can generate data useful for diagnostic' and research purposes.

Still another object of the present invention is to provide a device that is easy to install on a supporting base.

Still another object of the present invention is to provide a device that is easy to use.

Still another object of the present invention is to provide a device that can be used to perform certain yogic breathing practice using alternate nostrils, both nostrils or a single nostril.

Still another object of the present invention is to provide a device that automates and synchronizes the device with the patterns of human breathing.

Still another object of the present invention is to measure the force of human breath, an important diagnostic input for yoga experts.

In an embodiment of the present invention, the device includes one or more motion elements, one or more mechanical levers, and one or more pads. One or more attributes of the device is controlled by a controlling unit. The motion element is switched on and off based on the desired setting of the controlling unit. The motion element generates mechanical motion based on the signal from the controlling unit. The mechanical lever moves between the retracted position and the extended position with the state of the motion element. When the motion element is switched off, the mechanical lever is at rest at retracted position. When the motion element is switched on, the mechanical lever moves forward in the extended position, blocking the respective nostril. Thereafter the motion element is switched off, for a required duration; mechanical lever is locked in the extended position, still blocking the nostril. The motion element is switched on with reverse phase. Mechanical lever moves back and comes at rest in retracted position, unblocking the nostril.

The features of the invention believed to be novel are set forth with particularity in the appended claims. However the invention itself, both as to organization and method of manufacturing, together with further objects and advantages thereof may be best be understood by reference to the following description taken in conjunction with the accompanying drawings.

BRIEF DESCRIPTION OF THE DRAWINGS

Example embodiments of the present invention are illustrated by way of example and not limitation in the figures of the accompanying drawings, in which like references indicate similar elements and in which.

Figure 1:
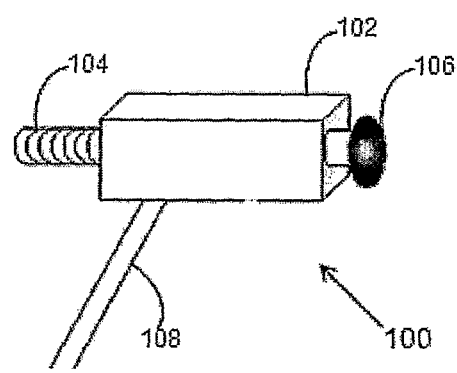
FIG. 1 illustrates a blown up view of device 100, in accordance with an embodiment of the present invention.

Other features of the present embodiments will be apparent from the accompanying drawings and from the detailed description that follows.

DETAILED DESCRIPTION

A Yoga device for performing certain yogic breathing practices onto the parts of the human body and a method for manufacturing the device are disclosed. In the following description, for purposes of explanation, numerous specific details are set forth in order to provide a thorough understanding of the various embodiments. It will be evident, however, to one skilled in the art, that the various embodiments may be practiced without these specific details. It will be appreciated that the various embodiments discussed herein may/may not be the same embodiment, and may be grouped into various other embodiments not explicitly disclosed herein.

The yoga device effectively helps in performing the certain ancient yogic breathing practices, such as anulom vilom pranayam, without involving the use of hands. The device may also be termed as a breath-a-healer. The device can be configured to get support from a supporting base. Examples of the supporting base include, but not limited to, the frames of a spectacle (shown in FIGS. 3, 7, 8A, 8B, and 10). One or more attributes of the device; such as number of cycles to be performed; can be controlled by a controlling unit (shown in FIG. 9). In an embodiment of the present invention, the device includes one or more motion elements, one or more mechanical levers, and one or more pads. The motion elements generate mechanical motion. Examples of the motion elements include, but not limited to, squiggle motors designed by New Scale Technologies USA (shown in FIGS. 1, 2A-2C, 5, and 6), or muscle wire (shown in FIGS. 7, 8A and 8B). Examples of the mechanical motion include, but not limited to, a linear motion. The device is coupled to the supporting base through the motion elements. The motion elements are connected to the controlling unit through one or more first connecting elements. Examples of the first connecting elements include, but not limited to, a coaxial cable or other wires or wireless.

The mechanical levers (shown in FIGS. 1, 2A-2C, 5, 6A-6C, 7, 8A and 8B) are coupled to the motion elements. The mechanical levers carry the mechanical motion generated by the motion elements. The mechanical levers move with the mechanical motion of the motion elements. The mechanical levers may include one or more lever ends, such as a first lever end and a second lever end (not shown). The pads (shown in FIGS. 1, 2A-2C, 5, 6A-6C, 7, 8A and 8B) are coupled to at least one of the lever ends of the mechanical levers. The pads work as artificial fingers. The pads interface with the parts of the human body. The device may further include one or more sensors (shown in FIG. 10) for sensing the breathing behavior and patterns and measuring the force of human breath. The sensors are coupled to the supporting base through one or more flexible elements. Examples of the flexible elements include, but not limited to, PVC insulated single core wire. The sensors are connected to the controlling unit through one or more second connecting elements. The examples of the second connecting elements include, but not limited to, a coaxial cable or other wires or wireless.

The controlling unit may include a control module, a data management module, and a power module. The control module may include one or more input buttons, and one or more output elements, such as a LCD panel. The input buttons may be used to input the required value of the attributes of the device. The output elements may display the output of the input. The control module, the data management module, and a power module are internally connected through one or more third connecting elements. Examples of the third connecting elements include, but not limited to, a coaxial cable or other wires or wireless. The power module may include one or more power source, such as a battery. The power source supplies power to each components of the device through one or more fourth connecting elements, such as an electrical wire. Data management module may collect, store, retrieve and disburse the data generated by the device.

The device can be integrated with a supporting base, such as the frames of the common spectacle that rests on the nose. In an example, two devices, such as a first device and a second device, are integrated on the frame of a common spectacle through their respective motion elements. The first device is fixed on right side of the frame through the first motion element whereas the second device is fixed on left side of the frame through the second motion element. In an example of the working mechanism, when the motion elements of both devices are switched off, the mechanical levers of the devices are at retracted positions and thus both nostrils of the nose are open. When the motion element of first device is switched on and the motion element of the second device is still switched off, the mechanical lever of the first device moves forward and presses the right nostril by its pad, blocking the right nostril.

Thereafter the motion element of first device is switched off for a required duration. The mechanical lever of the first device is locked in the extended position, blocking the right nostril. Thereafter the motion element of the first device is switched on with reverse phase. The mechanical lever of the first device moves back in retracted position, releasing the right nostril. The motion element of first device is switched off for a required duration. The mechanical lever of the first device is locked in the retracted position, unblocking the right nostril. Simultaneously the motion element of the second device is switched on. The mechanical lever of the second device moves forward and presses the left nostril by its pad, blocking the left nostril. Thereafter the motion element of the second device is switched off for a required duration. The mechanical lever of the second device is locked in the extended position, blocking the left nostril. Thereafter the motion element of the second device is switched on with reverse phase. The mechanical lever of the second device moves back in retracted position, releasing the left nostril. The motion element of the second device is switched off for a required duration. The mechanical lever of the second device is locked in the retracted position, unblocking the left nostril. These steps are repeated up to a desired number of cycles for the yogic breathing practice.

The motion elements can be controlled separately, and one may program the controlling unit to selectively block one nostril only, as may be required by specific yogic breathing practice.

The device can be manufactured in various methods in various embodiments, hi an embodiment of method of the present invention, the first step includes coupling the mechanical lever to the motion element. The second step includes coupling the pads to the mechanical lever. The method may further include coupling one or more sensors to the supporting base. Details of these applications have been provided in conjunction with drawings below.

Figure 2A:
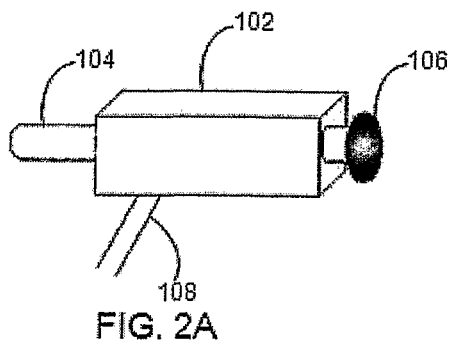
FIGS. 2A-2C illustrate how the mechanism of device 100 of FIG. 1 works, in accordance with an embodiment of the present invention.
Figure 2B:
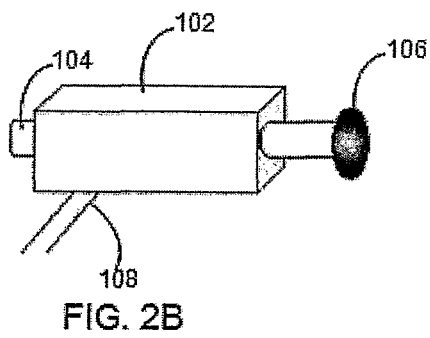
Figure 2C:
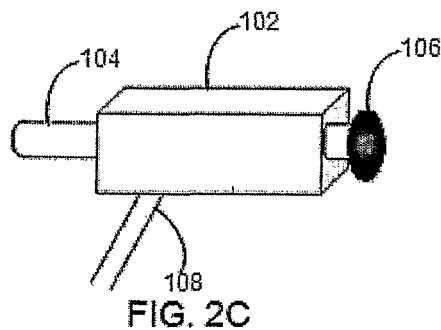

FIG. 1 illustrates a blown up view of device 100, in accordance with an embodiment of the present invention. Device 100 includes a motion element 102, a mechanical lever 104, and pad 106. Mechanical lever 104 is coupled to motion element 102. Device 100 further includes a first connecting element 108 for connecting motion element 102 to the controlling unit. Mechanical lever 104 includes one or more lever ends, such as a first lever end and a second lever end (not shown). Pad 106 is coupled to the second lever end of mechanical lever 104. Mechanical lever 104 in the extended position presses the nostril of the human nose by pad 106. Motion element 102 is connected to the controlling unit through first connecting element 108. FIGS. 2A-2C illustrate how the mechanism of device 100 of FIG. 1 works, in accordance with an embodiment of the present invention. Mechanical lever 104 moves between the retracted position and the extended position with the changes in the state (switched on or switched off) of motion element 102. Pad 106 moves along with mechanical lever 104 between the, retracted position and the extended position. As in FIG. 2A, when motion element 102 is switched off, mechanical lever 104 is at rest at the retracted position. In FIG. 2B, when motion element 102 is switched on, mechanical lever 104 moves forward in the extended position. Thereafter motion element 102 is switched off for a required duration; mechanical lever 104 is locked in the extended position. Thereafter motion element 102 is switched on with reverse phase, as in FIG. 2C. Mechanical lever 104 moves back and comes at rest in the retracted position.

Figure 3:
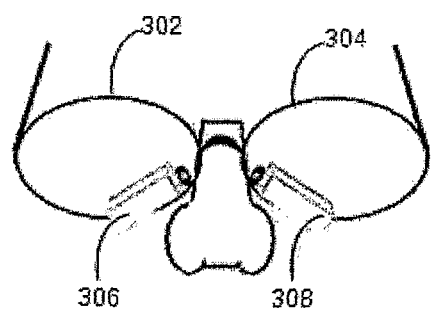
FIG. 3 illustrates devices 306 and 308, integrated on supporting bases 302 and '304, in accordance with an embodiment of the present invention.

FIG. 3 illustrates the devices 306 and 308 integrated on supporting bases 302 and 304, in accordance with an embodiment of the present invention. Devices 306 and 308 are integrated on supporting bases 302 and 304 respectively. Supporting bases 302 and 304 are the frames of a common spectacle that rests on the human nose. Device 306 is coupled to right frame 302 through its motion element whereas device 308 is coupled to left frame 304 through its motion element.

FIGS. 4A, 4B, 4C, and 4D illustrate how devices 306 and 308 emulate one cycle of the artificial yogic practice, in accordance with an embodiment of the present invention. Two motion elements, such as the motion element of device 306 and the motion element of device 308, are used as micro-actuators for the yogic practice. The pair of devices 306 and 308 operate to move between a first state and a second state, as will be described. The mechanical levers of the devices 306 and 308 move between the retracted position and the extended position with the change in the state (switched on or switched off) of their respective motion elements. As in FIG. 4A, the motion element of device 306 and the motion element of device 308 are switched off. The mechanical lever of device 306 and the mechanical lever of device 308 are at the retracted position, keeping both nostrils open.

Figure 4A:
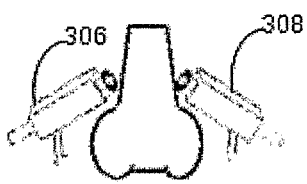
FIGS. 4A-4D illustrate how devices 306 and 308, emulate one cycle of the artificial yogic practice, in accordance with an embodiment of the present invention.
Figure 4B:
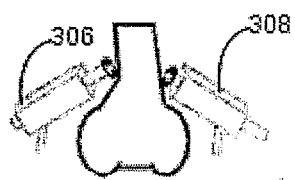
Figure 4C:
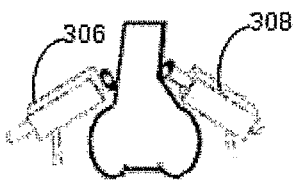
Figure 4D:
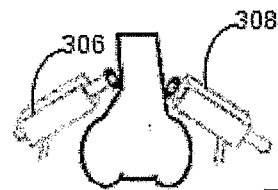

The configuration of the devices 306 and 308 in the first state is shown in FIGS. 4B and 4D. In FIG. 4B, the motion element of device 306 is switched on, the mechanical lever of device 306 moves in the extended position and presses the right nostril with its coupled pad. The right nostril is blocked while the left nostril is still open. The motion element of device 306 is switched off for a required duration; the motion element of device 306 is locked in the extended position, blocking the right nostril. The configuration of the devices 306 and 308 in the second state is shown in FIG. 4C. In FIG. 4C, the motion element of device 306 is switched on with reverse phase. The mechanical lever of device 306 moves back and releases the right nostril. Thereafter the motion element of device 306 is switched off again; now the mechanical lever of device 306 is locked in the retracted position, unblocking the right nostril.

Simultaneously the motion element of device 308 is switched on; the mechanical lever of device 308 moves forward in the extended position and presses the left nostril with its coupled pad. The left nostril is now blocked while the right nostril is open. The motion element of device 308 is switched off for a required duration; the mechanical lever of device 308 is locked in the extended position, blocking the left nostril. The configuration of the devices 306 and 308 in FIG. 4C corresponds to the second state. In FIG. 4D, the motion element of device 308 is switched on with reverse phase; the mechanical lever of device 308 moves back in the retracted position, releasing the left nostril. The motion element of device 308 is switched off again for a required duration; the mechanical lever of device 308 is locked in the retracted position, unblocking the left nostril.

Simultaneously the motion element of device 306 is switched on; the mechanical lever of device 306 moves forward in the extended position and presses the right nostril with its coupled pad. The right nostril is now blocked while the left nostril is open. Thereafter the motion element of device 306 is switched off for a required duration; the mechanical lever of device 306 is locked in the extended position, blocking the right nostril. The steps of FIG. 4A-4D (i.e., movement between the first and second states) are repeated for a specified number of cycles for performing the yogic practice.

Figure 5:
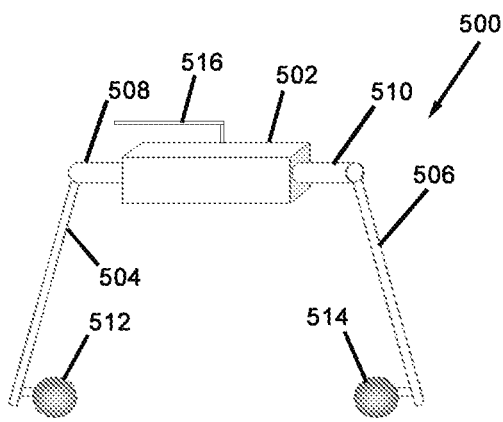
FIG. 5 illustrates a blown up view of device 500, in accordance with an embodiment of the present invention.

FIG. 5 illustrates a blown up view of device 500, in accordance with an embodiment of the present invention. Device 500 includes a motion element 502, one or more mechanical levers, such as a mechanical lever 506 and a mechanical lever 506, and one or more pads, such as a pad 512 and a pad 514. Device further includes a first connecting element 516 for connecting motion element 502 to the controlling unit. Device may further include one or more motion supporting elements, such as a first motion supporting element 508 and a second motion supporting element 510, for supporting the coupling of mechanical levers 504 and 506 to motion element 502. Mechanical levers 504 and 506 are coupled to motion element 502 with motion supporting elements 508 and 510 respectively. Pads 512 and 514 are coupled to mechanical lever 504 and mechanical lever 506 respectively.

Figure 6A:
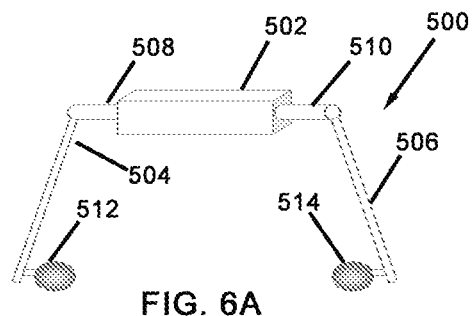
FIGS. 6A-6C illustrate how the mechanism of device 500 of FIG. 5 works, in accordance with an embodiment of the present invention.
Figure 6B:
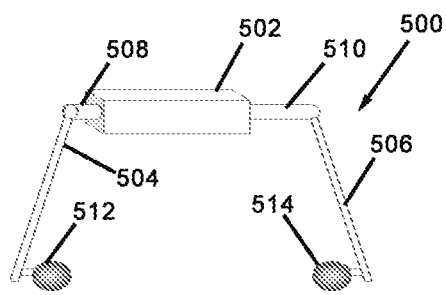
Figure 6C:
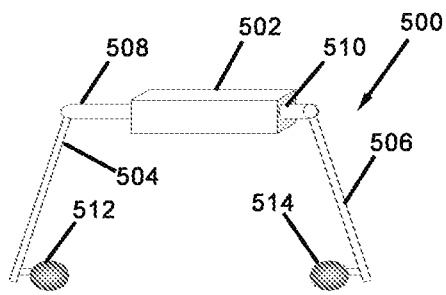

FIGS. 6A, 6B, and 6C illustrate how the mechanism of device 500 of FIG. 5 works, in accordance with an embodiment of the present invention. Mechanical levers 504 and 506 move among rest position, right position, and left position with the changes in the state (switched on and switched off) of motion element 502. In the rest position of mechanical levers 504 and 506, both of the nostrils, such as a right nostril and a left nostril, are open. In the right position of mechanical levers 504 and 506, the right nostril is blocked while the left nostril is open. In the left position of mechanical levers 504 and 506, the left nostril is blocked while the right nostril is open. As in FIG. 6A, motion element 502 is switched off; mechanical levers 504 and 506 are in the rest position, unblocking the both nostrils.

In FIG. 6B, motion element 502 is switched on; mechanical levers 504 and 506 move in the right position; blocking the right nostril. The left nostril is still open. Thereafter motion element 502 is switched off for a required duration; mechanical levers 504 and 506 are locked in the right position, blocking the right nostril. As in FIG. 6C, motion element 502 is switched on with reverse phase; mechanical levers 504 and 506 move in the left position, releasing the right nostril and simultaneously blocking the left nostril. Thereafter motion element 502 is switched off for a required duration; mechanical levers 504 and 506 are locked in the left position, blocking the left nostril. The steps of FIG. 6A-6C are repeated for a specified number of cycles for performing the yogic practice.

Figure 7:
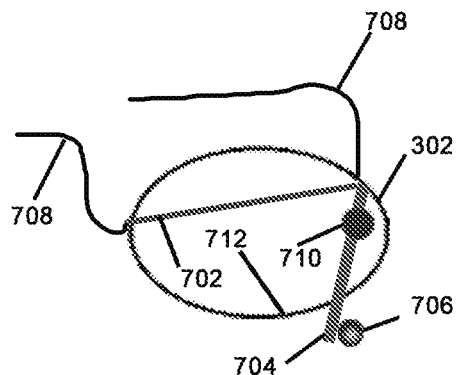
FIG. 7 illustrates a device integrated on supporting base 302, in accordance with another embodiment of the present invention.

FIG. 7 illustrates a device integrated on supporting base 302, in accordance with another embodiment of the present invention. The device includes a motion element 702, a mechanical lever 704, a pad 706, and an elastic element 712. Motion element 702, such as muscle wire or shape memory actuators, includes one or more motion ends, such as a first motion end and a second motion end (not shown). The first motion end is coupled to supporting base 302. Motion element 702 generates mechanical motion by contracting and stretching when it is heated up or when a specific electrical current is passed through it. The device is supported on supporting base 302 through motion element 702. Motion element 702 is connected to the controlling unit through one or more fifth connecting elements 708. Examples of the fifth connecting elements include, but not limited to, a coaxial cable or other wires or wireless. The fifth connecting elements 708 are connected at both ends of motion element 702. Mechanical lever 704 may include one or more lever ends, such as a first lever end and a second lever end (not shown). The first lever end of mechanical lever 704 is coupled to motion element 702 at the second motion end.

Mechanical lever 704 carries the mechanical motion generated by motion element 702 to pad 706. Mechanical lever 704 is further coupled to supporting base 302 through elastic element 712. Elastic element 712 includes one or more ends, such as a first elastic end and a second elastic end (not shown). Elastic element 712 engages elastically mechanical lever 704 to supporting base 302. Elastic element 712 stretches and contracts based on the movement of mechanical lever 704. Elastic element 712 is coupled to supporting base 302 at first elastic end whereas it is coupled to mechanical lever 704 at second elastic end. The device may further include a pivoting element 710, such as a pivot, for affirming the movement of mechanical lever 704. Pad 706 is coupled to second lever end of mechanical lever 704.

Mechanical lever 704 moves between the retracted position and the extended position with the mechanical motion of motion element 702. When the specific electrical current passes through motion element 702, motion element 702 contracts and thus mechanical lever 704 moves in the extended position, and elastic element 712 is stretched. When the supply of the electrical current is removed, motion element 702 stretches to its original state, mechanical lever 704 moves in the retracted position with elastic element 712. Mechanical lever 704 is pivoted onto supporting base 302 through pivoting element 710.

Figure 8A:
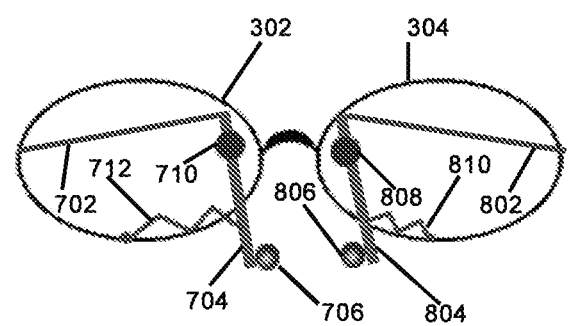
FIGS. 8A and 8B illustrate how the mechanism of the device of FIG. 7 works, in accordance with an embodiment of the present invention.
Figure 8B:
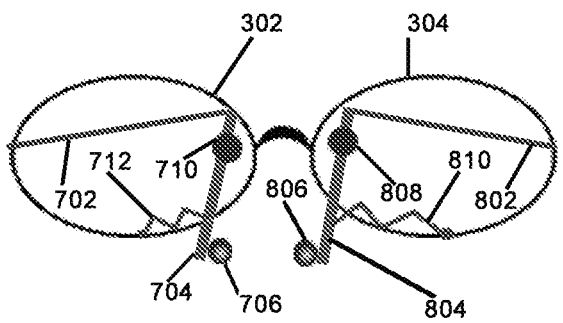

FIGS. 8A and 8B illustrate how the mechanism of the device of FIG. 7 works, in accordance with an embodiment of the present invention. When electrical current passes through motion element 702 onto supporting base 302, motion element 702 contracts, as shown in FIG. 8A. First lever end of mechanical lever 704 is pulled towards motion element 702, mechanical lever 704 moves in the extended position, blocking the right nostril. Elastic element 712 is stretched as it is engaged to mechanical lever 704. When the supply of the electrical current is removed, motion element 702 relaxes and stretches to its original state, stretched elastic element 712 pulls mechanical lever 704 by second lever end of mechanical lever 704 towards itself. Thus mechanical lever 704 moves in the retracted position, unblocking the right nostril.

Simultaneously electrical current is passed through motion element 802 on supporting base 304, motion element 802 contracts, as shown in FIG. 8B. First lever end of mechanical lever 804 is pulled towards motion element 802, mechanical lever 804 moves in the extended position, blocking the left nostril. Elastic element 810 is stretched as it is engaged to mechanical lever 804. When the supply of the electrical current is removed, motion element 802 relaxes and stretches to its original state, stretched elastic element 810 pulls mechanical lever 804 by second lever end of mechanical lever 804 towards itself. Thus mechanical lever 804 moves in the retracted position, unblocking the left nostril. Pivoting elements 710 and 808 affirm the movement of mechanical levers 704 and 804 from the retracted position to the extended position on supporting bases 302 and 304 respectively. The steps of FIG. 8A-8B are repeated for a specified number of cycles for performing the yogic practice.

Figure 9:
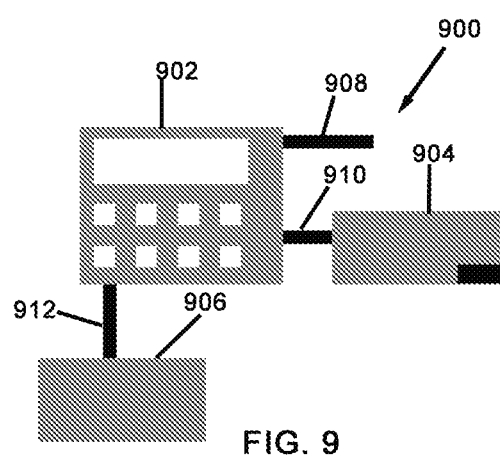
FIG. 9 illustrates diagrammatic view of controlling unit 900, in accordance with an embodiment of the present invention.

FIG. 9 illustrates diagrammatic view of an electronic controlling unit 900, in accordance with an embodiment of the present invention. Electronic controlling unit 900 includes a control module 902, a data management module 904, and a power module 906. Control module 902 may include one or more input buttons, and an output panel, such as a LCD panel. The input buttons may be used to input required values for controlling the one or more attributes of the device. For example, the input buttons may be used to enter the number of cycles to perform the desired yogic practice, switched on or switched off the motion element. The output panel may display the values of the input and/or output. Data management module 904 may collect, store, retrieve and disburse the data of the device. Data management module 904 may include one or more external data ports, such as IEE 1394. Power module 906 may include one or more power source, such as a battery. Power module 906 supplies power to each components of the device. Control module 902, data management module 904, and power module 906 may be internally connected with each other through one or more third connecting elements 908, 910, and 912. Examples of third connecting elements 908, 910, and 912 include, but not limited to, wire or wireless. Electronic controlling unit 900 may be programmed for desired need.

Figure 10:
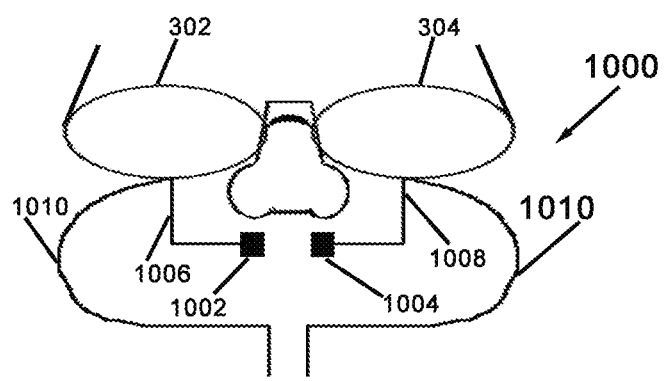
FIG. 10 illustrates arrangement of sensors 1002 and 1004 on supporting bases 302 and 304, in accordance with an embodiment of the present invention.

FIG. 10 illustrates arrangement of sensors 1002 and 1004 on supporting bases 302 and 304, in accordance with an embodiment of the present invention. Sensors 1002 and 1004 are coupled to supporting bases 302 and 304 through one or more flexible elements 1006 and 1008. Sensor 1002 is adjusted under right nostril while sensor 1004 is adjusted under left nostril. Sensors 1002 and 1004 are connected to the controlling unit through one or more second connecting elements 1010. Sensors 1002 and 1004 monitor the breathing behavior and/or the breathing position of the human nostrils. Sensors 1002 and 1004 may sense the force and flow of the breath into and out of each nostril and may automate and synchronize the movement of mechanical levers to the normal breathing of the human nostrils. The sensors also measure the force of breath.

The device may be manufactured in various ways in various embodiments. In an embodiment of the present invention, the first step of the method includes connecting one or more motion elements to a controlling unit through one or more first connecting elements. The second step includes coupling one or more mechanical levers to the motion elements. The mechanical levers carry the mechanical motion. The mechanical levers may include one or more lever ends. The third step includes coupling one or more pads to at least one of the lever ends. The pads interface with the parts of the human body.

The fourth step includes coupling one or more sensors to the supporting base. The sensors sense the breathing behavior and patterns while measuring the force of breath. The fifth step includes connecting the sensors to the controlling unit through one or more second connecting elements.

In another embodiment of the present invention, the first step of the method includes connecting one or more motion elements to a controlling unit through one or more first connecting elements. The second step includes coupling one or more mechanical levers to the motion elements. The mechanical levers carry the mechanical motion, the mechanical levers may include one or more lever ends. The third step includes coupling one or more pads to at least one of the lever ends. The pads interface with the parts of the human body. The fourth step includes coupling one or more sensors to the supporting base. The sensors sense the breathing behavior and patterns while measuring the force of breath. The fifth step includes connecting the sensors to the controlling unit through one or more second connecting elements. The sixth step includes coupling at least on of one or more elastic ends of one or more elastic elements to the supporting base. The seventh step includes coupling at least one of remaining of elastic ends to the mechanical levers. The elastic elements engage the mechanical levers to the supporting base. The seventh step includes coupling one or more pivoting elements on the supporting base for affirming the movement of the mechanical levers from the retracted position to the extended position. The device may be integrated to the supporting base through the motion elements.

In addition, it will be appreciated that the various operations, processes, and methods disclosed herein may be performed in any order. Accordingly, the specification and drawings are to be regarded in an illustrative rather than a restrictive sense.

The invention claimed is:

1. A yogic breathing device comprising:
   one or more motion elements for generating mechanical motion, the motion elements including one or more first connecting elements, and the motion elements being integrated on a supporting base configured to be worn on the face of a user;
   one or more mechanical levers mechanically coupled to the motion elements for carrying the mechanical motion generated by the motion elements, the mechanical levers comprising one or more lever ends;
   an electronic controlling unit operatively coupled to the motion elements through the first connecting elements of the motion elements, the electronic controlling unit configured to actuate the motion elements; and
   one or more pads, at least one of the pads being coupled to at least one of the lever ends of the mechanical levers, the pads configured to be pressed on the nostrils of the user in response to actuation of the motion elements by the electronic controlling unit.

2. The device of claim 1, further comprising one or more sensors for sensing breathing habits and patterns of the user, and measuring the force of breath of the user, the sensors being coupled to the supporting base through one or more flexible elements, the sensors being connected to the controlling unit through one or more second connecting elements.

3. The device of claim 1, wherein the first connecting elements is a wire or wireless.

4. The yogic breathing device of claim 1, wherein the electronic controlling unit is configured to actuate the motion elements to move between a first state, in which the one or more mechanical levers are retracted such that the pads are spatially separated from the nostrils of the user, and a second state, in which the one or more mechanical levers are extended such that the pads contact nostrils of the user.

5. A yogic breathing arrangement supportable by a supporting base configured to be worn by a user, the yogic breathing arrangement comprising:
   a first yogic device and a second yogic device, each of the yogic devices comprising:
      a motion element integrated on the supporting base, the motion element for generating mechanical motion and including a connecting element,
      a mechanical lever mechanically coupled to the motion element for carrying the mechanical motion generated by the motion element, the mechanical lever including a lever end, and
      a pad coupled to the lever end; and
   an electronic controlling unit operatively coupled to the motion elements through the respective connecting elements of the motion elements, the electronic controlling unit configured to actuate the motion elements to move between a first state, in which the mechanical lever of the second yogic breathing device is retracted and the mechanical lever of the first yogic breathing device is extended causing the pad of the first yogic breathing device to be configured to contact a first region of the nose of the user, and a second state, in which the mechanical lever of the first yogic breathing device is retracted and the mechanical lever of the second yogic breathing device is extended causing the pad of the second yogic breathing device to be configured to contact a second region of the nose of the user.

6. A yogic breathing device supportable by a supporting base, the yogic breathing device comprising:
   one or more motion elements for generating mechanical motion, the motion elements being connected to a controlling unit through one or more first connecting elements, the yogic breathing device being integrated on the supporting base through the motion elements;
   one or more mechanical levers mechanically coupled to the motion elements for carrying the mechanical motion generated by the motion elements, the mechanical levers comprising one or more lever ends;
   one or more pads for interfacing with parts of a human body, at least one of the pads being coupled to at least one of the lever ends of the mechanical levers; and
   one or more sensors for sensing breathing habits and patterns of the human body, and measuring the force of breath of the human body, the sensors being coupled to the supporting base through one or more flexible elements, the sensors being connected to the controlling unit through one or more second connecting elements.

* * * * *